United States Patent [19]

Ressler et al.

[11] Patent Number: 5,626,768
[45] Date of Patent: May 6, 1997

[54] STERILIZATION OF OPAQUE LIQUIDS WITH ULTRAVIOLET RADIATION

[75] Inventors: Barry Ressler, Weston, Conn.; Gary L. Morgan, Elkridge, Md.; Richard J. Herbermann, Huntington, N.Y.; David A. Wright, Solomons, Md.; James E. Stangroom, Sheffield, United Kingdom

[73] Assignee: Triton Thalassic Technologies, Inc., Ridgefield, Conn.

[21] Appl. No.: 569,830

[22] Filed: Dec. 7, 1995

[51] Int. Cl.⁶ .................................................. C02F 1/32
[52] U.S. Cl. ........................... 210/748; 210/192; 250/435; 250/437
[58] Field of Search ................ 250/432 R, 436, 250/437, 438; 210/748, 192; 422/24

[56] References Cited

U.S. PATENT DOCUMENTS

| | | | |
|---|---|---|---|
| 1,193,143 | 8/1916 | Henri et al. | 250/437 |
| 1,196,481 | 8/1916 | Von Recklinghausen | 250/437 |
| 1,266,803 | 5/1918 | Henri et al. | 250/437 |
| 1,473,095 | 4/1923 | Henri et al. | 250/437 |
| 2,577,879 | 12/1951 | Stoutz | 250/437 |
| 3,079,498 | 2/1963 | Ruffin | 250/437 |
| 3,138,708 | 6/1964 | Ellner et al. | 250/437 |
| 3,246,144 | 4/1966 | Beall et al. | 250/436 |
| 3,264,055 | 8/1966 | Barker | 250/436 |
| 3,757,495 | 9/1973 | Sievers | 55/279 |
| 4,296,066 | 10/1981 | Schenck | 250/437 |
| 4,320,085 | 3/1982 | Takeguchi et al. | 250/436 |
| 4,323,810 | 4/1982 | Horstmann | 250/436 |
| 4,857,204 | 8/1989 | Joklik | 210/695 |
| 4,963,750 | 10/1990 | Wilson | 250/436 |
| 4,968,891 | 11/1990 | Jhawar et al. | 250/436 |
| 5,063,030 | 11/1991 | Sweetman | 422/189 |
| 5,136,170 | 8/1992 | Gellert | 250/492.1 |
| 5,151,252 | 9/1992 | Mass | 422/186.3 |
| 5,320,749 | 6/1994 | Mullen | 210/199 |
| 5,343,114 | 8/1994 | Beneking et al. | 313/485 |
| 5,352,359 | 10/1994 | Nagai et al. | 210/192 |
| 5,393,419 | 2/1995 | Tiede et al. | 210/192 |
| 5,395,522 | 3/1995 | Melanson et al. | 210/202 |
| 5,413,768 | 5/1995 | Stanley, Jr. | 422/186.3 |
| 5,449,466 | 9/1995 | Peebles, III et al. | 210/747 |

OTHER PUBLICATIONS

International Waterguard Industries of Canada Product Bulletin, May 16, 1995.
Heraeus Amersil Product Bulletin.
Perry's Chemical Engineer's Handbook, 6th Ed. (1984) pp. 5-6, 5-26, 5-27, 5-28.

Primary Examiner—Cynthia L. Nessler
Attorney, Agent, or Firm—Martin Fruitman

[57] ABSTRACT

An apparatus and a method for killing bacteria within an opaque liquid. The opaque liquid is moved along a high power ultraviolet radiation surface at a velocity which causes turbulent flow in the liquid. The turbulent flow mixes the opaque liquid so that all the liquid is exposed to the radiation even though the radiation does not penetrate the liquid to any significant depth. One embodiment of the invention moves the liquid in a serpentine path between multiple planar lamps which radiate UV from both planar surfaces.

7 Claims, 5 Drawing Sheets

STERILIZATION OF OPAQUE LIQUIDS WITH ULTRAVIOLET RADIATION

BACKGROUND OF THE INVENTION

This invention deals generally with the use of ultraviolet radiation to sterilize liquids and more specifically with an apparatus and method to kill bacteria in a fluid which is essentially opaque to ultraviolet radiation.

The exposure of liquids to ultraviolet radiation in order to sterilize them by killing bacteria is a long established technique. Many patents have been issued which are based on the ability of ultraviolet radiation to destroy bacteria, and such devices are common enough to be in use in many households and industries. Typically, such systems expose water to ultraviolet radiation by passing the water through an enclosure in which it is exposed to ultraviolet radiation. In some such devices the water is routed around a cylindrical lamp by directing it a spiral path, thus increasing the time during which the water is exposed to radiation, and assuring a more complete kill of the bacteria within the water.

One consideration which pervades all the prior art and is so well accepted that it is rarely even mentioned is that the treatment of water by exposure to ultraviolet radiation depends upon the water itself being significantly transparent to the ultraviolet radiation. The penetration of ultraviolet radiation through water typically may range from a few inches to more than a foot. Without such transparency to ultraviolet radiation, the purification of the water is very difficult because only the surface of the water in actual contact with the source of radiation is affected by the ultraviolet radiation. In fact, several patents on the subject suggest prefiltering the water to remove particles before treating it with ultraviolet radiation.

However, there are some applications in which it is required that fluids which are opaque to ultraviolet radiation be treated to kill bacteria. One such application is for the treatment of industrial cooling fluids such as oil and water emulsions in which bacteria must be destroyed to prevent threats to human health, deterioration of the coolant fluid, and the generation of noxious odors.

Another application which is more familiar to most people, and for which ultraviolet radiation has not been generally used, is the treatment of sewage. In both of these applications the fluid is essentially opaque and the use of ultraviolet radiation has been given little consideration. The accepted treatment for such applications has been the use of chemical biocides to inhibit the growth of or destroy bacteria. Unfortunately, the use of chemical biocides presents other problems. While the chemical biocides have been generally successful in destroying bacteria, they are also dangerous to humans and other animal life. Chemical biocides therefore pose a hazard in the industrial environment and create a significant problem in regard to disposal at the end of the useful life of the fluids with which they are used.

Therefore, it would highly desirable to have available a device which can use ultraviolet radiation to kill bacteria in fluids which are essentially opaque to ultraviolet radiation.

SUMMARY OF THE INVENTION

The present invention is capable of treating opaque fluids with ultraviolet radiation and killing the bacteria within such opaque fluids. The invention is based upon the excimer type ultraviolet (UV) lamp which has been developed relatively recently. Such UV lamps depend upon what is sometimes called "silent electrical discharge", but their particular benefits are the ability to be constructed in planar and cylindrical configurations not possible with conventional mercury lamp technology and to operate at high intensities and high efficiencies. Moreover, excimer lamps can provide a high power density of ultraviolet radiation on their relatively large planar surfaces. Power densities of up to 1.0 watt/square centimeter have been acknowledged, and such power densities are more than ample to destroy bacteria on the surface of an opaque fluid in a very short time.

The present invention goes beyond the mere destruction of the bacteria in the surface layer of the opaque fluid. The fluid treatment apparatus of the invention uses a particular configuration of the UV exposure apparatus to kill bacteria in a large volume of opaque fluid which is flowing through the UV treatment apparatus at significant flow rates.

The first embodiment of the liquid treatment apparatus is constructed with an enclosed UV exposure apparatus which includes several interlaced, high power, planar UV sources through which the treated liquid flows in a short height serpentine path. The flow through the UV exposure apparatus is driven by a pump which receives liquid from a main reservoir containing contaminated fluid, and the sterilized liquid can either be delivered to a different reservoir, or, in a closed system it can be returned to the original reservoir.

Returning the purified fluid to the main reservoir to be remixed with contaminated fluid seems at first to be counter productive, but there are some circumstances in which it is very effective. For instance, in an application where a fluid is being used to cool operating machinery, the fluid is not discarded, but rather sterilized and returned for reuse. Furthermore, in many such circumstances, the requirement is not to kill all the bacteria in the whole system, but merely to prevent the contamination from reaching levels which make the fluid dangerous or unsuitable for use. Under such conditions it is enough to operate a bacteria reduction apparatus which at least reduces the bacteria in the fluid faster than bacteria growth replenishes it.

The goal in such applications need not be to completely eliminate bacteria, but to merely limit it. Such a goal can be met by long term operation of a system which kills the bacteria in a portion of the fluid and remixes the portion purified with the total quantity of fluid, thereby diluting the bacteria concentration in the entire fluid. The present invention can take advantage of that approach for control of the bacteria in large volumes of reusable fluid.

The basic approach of the present invention is to pass a small layer or "slice" of liquid within close proximity to a high power UV radiation source for a long enough time to kill the bacteria within the depth of the entire "slice". The length of treatment time is determined either by making the flow path of the liquid long enough to yield the exposure time required for killing bacteria, or by repeatedly circulating the liquid through a shorter flow path to reach the required exposure time. Furthermore, the liquid is subjected to turbulent flow so that the liquid is exposed to UV radiation to a greater effective depth than the mere surface layer, which would be all that would be treated if the opaque liquid flowed past the UV lamp as laminar flow.

The UV exposure apparatus of the first embodiment of the present invention is constructed as a rectangular prism vessel with multiple parallel rectangular planar radiation sources enclosed within the apparatus. Two opposite edges of all the planar radiation sources are sealed against opposite walls of the apparatus. The other opposite edges of alternate planar radiation sources are sealed to only one of the opposite sides of the apparatus. Thus, liquid entering the apparatus at the bottom flows across one face of the lowest planar lamp, and then back between the other face of lowest the lamp and the first face of the lamp above the lowest lamp. This flow pattern continues, with the liquid flowing in alternate directions, in a serpentine path, back and forth between the lamps, until it leaves the apparatus at the top.

This flow pattern creates a long flow path within a reasonable apparatus size, and since excimer UV lamps can be constructed with radiation emitting surfaces on both sides of a plane, it also permits the liquid to be exposed to radiation at both the top and bottom of each flow passage between the lamps.

However, the key to successful purification involves two other features of the apparatus. First, the height of the flow passages, the space between the lamps, must be small, but even then, since in highly opaque liquids the penetration of ultraviolet radiation is only a few monolayers deep, in order to expose the entire thickness of the liquid for the entire flow time through the fluid passage, the height of the flow passage would have to be impractically small. The solution to that problem is the creation of turbulence within the flow passages.

While it is theoretically possible to create turbulence in the liquid by using multiple deflectors, a more beneficial method of creating turbulent flow in the flow path is to increase the velocity of the liquid until the flow becomes turbulent. This approach yields two additional advantages. First, the higher velocity flow increases the amount of liquid treated within a given time period. Moreover, the high velocity turbulent flow also cools the UV lamps and maintains them within their operating temperature limits.

The basic function of the turbulent flow is, however, to constantly bring new liquid in contact with the surface of the lamps where the bacteria within the liquid is killed.

The first embodiment of the invention therefore is a simple box-like apparatus with multiple excimer planar lamps separated by by a flow path only two centimeters high, through which the opaque liquid flows and is sterilized. The excimer lamps yield the advantage of not only producing high power density, but they also produce monochromatic radiation and are available at several distinct wavelengths so that they can be selected for specific germicidal applications. Such lamps also require no ballasts, and no quartz shield for electrical isolation or temperature stabilization.

The fluid flow within the treatment vessel is determined by a treatment pump. This pump moves liquid through the treatment vessel at a rate that is independent of the liquid flow in the system using the liquid, and the treatment pump may move liquid through the treatment vessel several times before it is drawn out and into the main liquid system. This action effectively lengthens the exposure time of the liquid to UV radiation, and reduces the need for a longer flow path.

An alternate embodiment of the invention provides for independent adjustment of the flow into the UV exposure apparatus by using the main system pump and including a separate valve in a branch flow path to control the liquid flow through the UV exposure apparatus. Thus, the flow through the main system is determined by the pump, while the flow into the UV exposure apparatus is controlled by the independent valve.

The invention thereby furnishes a system which sterilizes opaque liquids without any chemical treatment, and can do so at flow rates independent of the use to which the fluid is put.

DETAILED DESCRIPTION OF THE INVENTION

Figure 1:
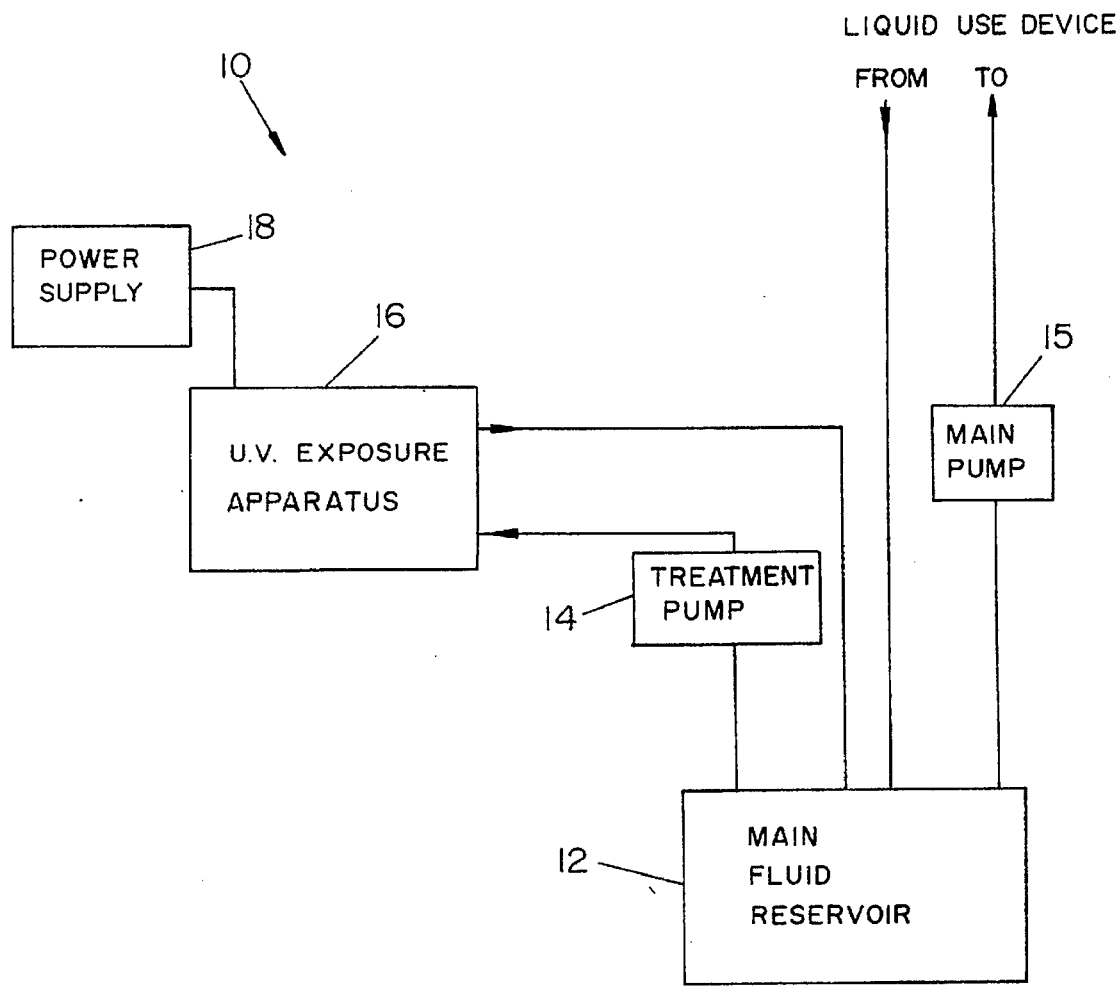
FIG. 1 is a simplified schematic diagram of the first embodiment of the invention.

FIG. 1 is a simplified schematic diagram of the first embodiment of the invention in which sterilization apparatus 10 includes main reservoir 12, treatment pump 14, main pump 15, UV exposure apparatus 16, and UV lamp power supply 18. Such an arrangement is most useful when it is desirable that the quantity of liquid being sterilized in the system, or the liquid flow required to produce the desired turbulent liquid velocity within UV exposure apparatus 16, be independent of the liquid flow used by the primary device in the system (not shown). Such a situation might easily arise when the liquid in the system is used in large quantities, but on a low duty cycle, that is, with short periods of flow and long intervals between flow periods. Under such circumstances, constant UV treatment of smaller quantities of liquid can be accomplished by the configuration of FIG. 1.

Figure 2:
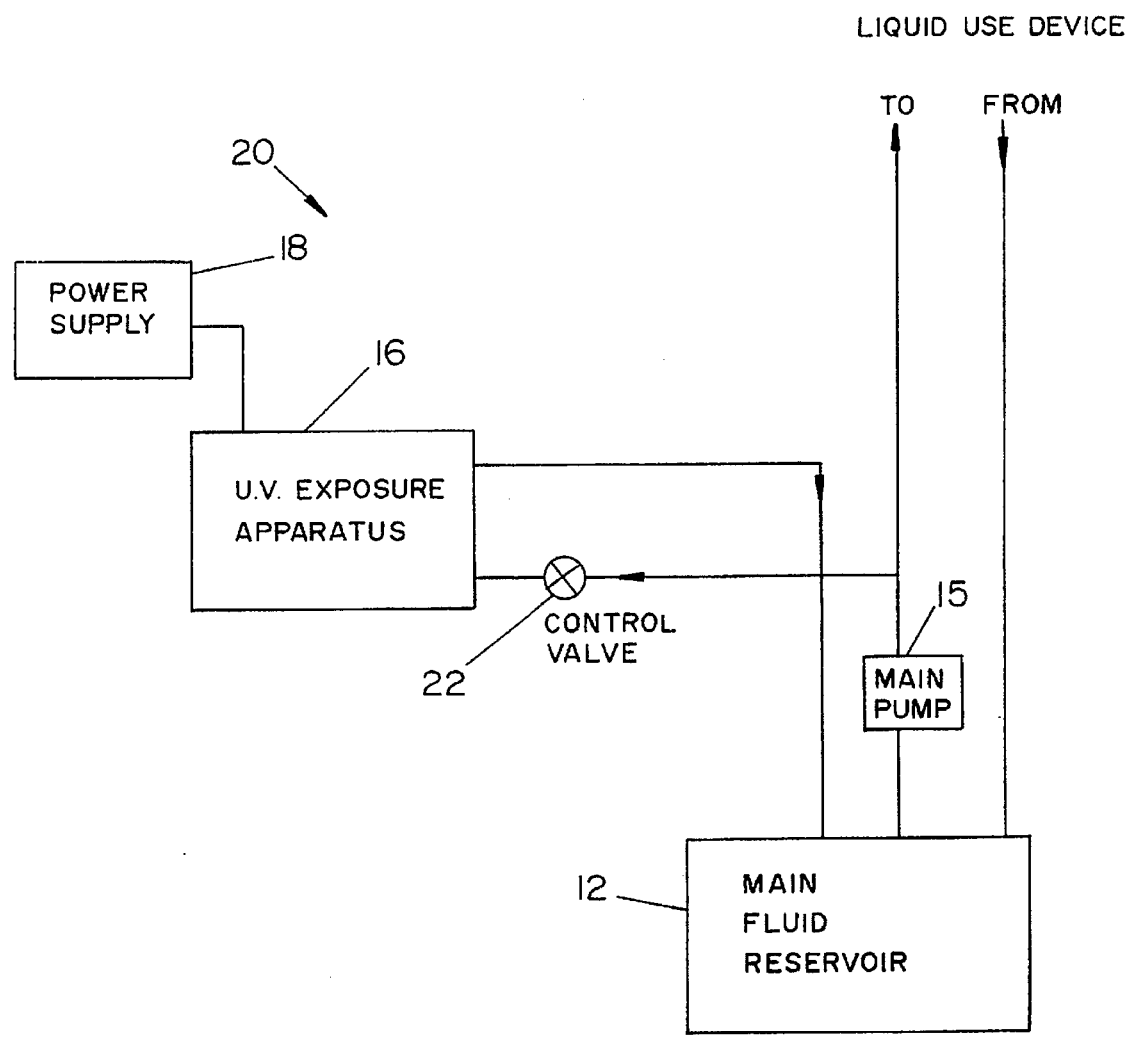
FIG. 2 is a simplified schematic diagram of an alternative embodiment of the invention which uses a separately valved branch flow path to control the fluid flow into the UV exposure apparatus.

FIG. 2 is a simplified schematic diagram of an alternative embodiment of the invention in which sterilization apparatus 20 uses main pump 15 and control valve 22 to control the liquid velocity through UV exposure apparatus 16. This configuration permits the liquid flow from main reservoir 12 to the liquid use device (not shown) to be substantially different from the liquid flow through the UV exposure apparatus, but the operation time of UV exposure apparatus 16 must be the same as main pump 15. Essentially, control valve allows liquid to flow through UV exposure apparatus 16 at whatever rate is required to yield the liquid velocity within UV exposure apparatus 16 which is most satisfactory for the specific liquid being treated, while main pump 15 delivers liquid for use in the system at some other desirable flow rate.

Figure 3:
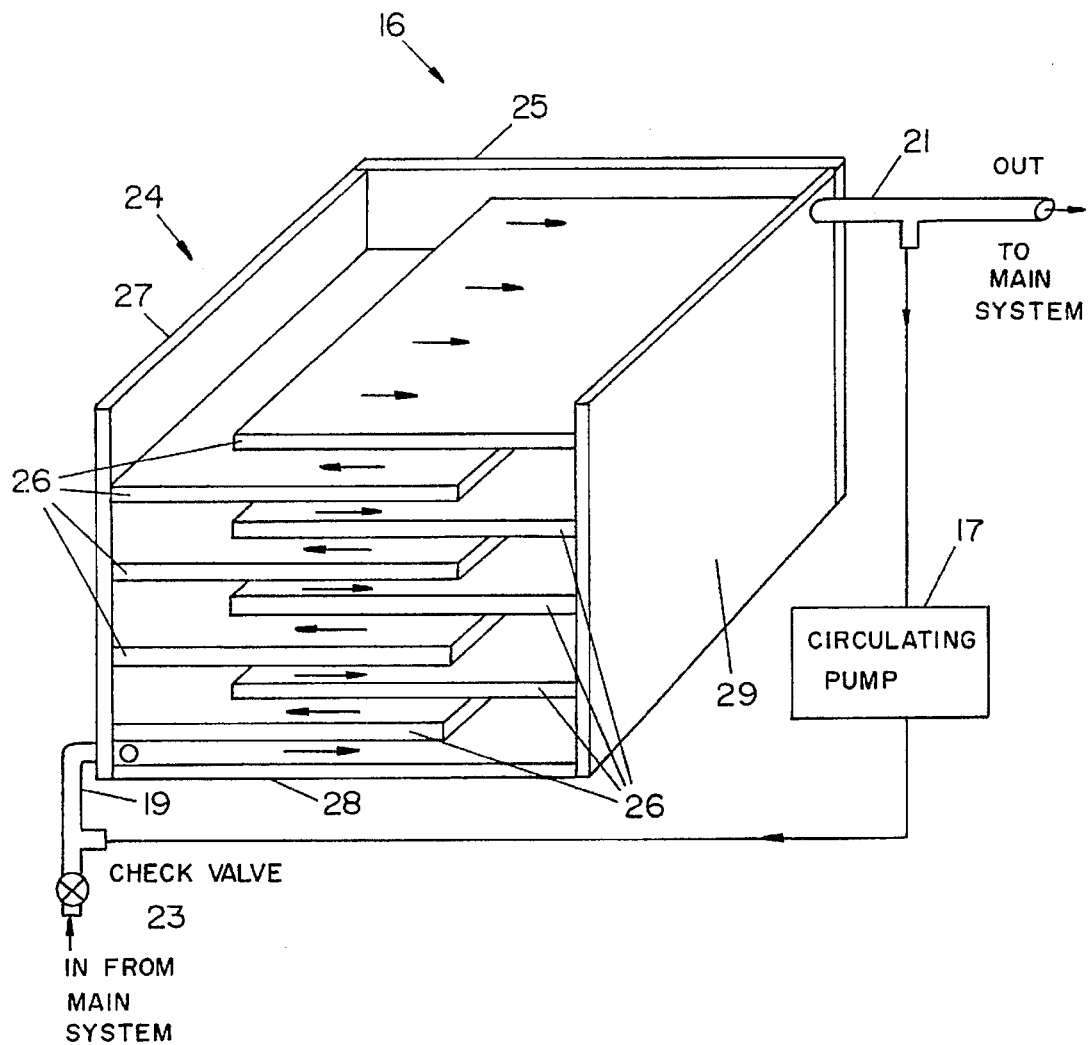
FIG. 3 is a simplified perspective view of one embodiment of the UV exposure apparatus of the first embodiment of the invention, with the top and one side of the box-like structure of the apparatus omitted to furnish a better view of the internal structure, and the treatment pump shown in schematic form.

FIG. 3 is a simplified perspective view of one embodiment of UV exposure apparatus 16 of the first embodiment of the invention in which treatment enclosure 24 is formed as a box-like rectangular prism of any suitable material, such as stainless steel, which will not react with the liquid being treated. The top and one side panel of enclosure 24 have been omitted to afford a better view of the simple internal structure of enclosure 24.

The internal structure of enclosure 24 is constructed with eight planar excimer lamps 26 sealed against side 25 and the opposite side (not shown), and with alternate lamps attached to sides 27 and 29. Lamps 26 are constructed with dimensions of 30 inches square and are spaced two centimeters apart and two centimeters from top and bottom panels 28. Similar lamps are described in U.S. Pat. No. 5,343,114 to Beneking et al and in a product bulletin by Heraeus Amersil of Duluth, Ga. The lamp spacings are selected on the assumption that the UV radiation does not penetrate the liquid. However, experimentation has demonstrated that the turbulence caused by the high velocity of flow and the long length of flow path causes all portions of the 1 centimeter thickness adjacent to each lamp surface to be sterilized as the liquid moves through enclosure 24.

Adjustments to the plate spacing and length of flow path may be required on the basis of such parameters as the quantity of liquid to be sterilized, the depth of penetration of UV radiation through the opaque liquid, the fluid flow velocity required to produce turbulent flow of the liquid, the flow required to remove heat from the lamp faces to prevent too high a lamp temperature, and the pump pressure required to provide such a flow.

Experimentation has shown that the turbulence required to constantly bring bacteria to the liquid surface for treatment requires a flow with a typical Reynolds number of 30,000. The treated liquid flows through enclosure 24 in a serpentine path as indicated by the arrows, and the lamps emit radiation from both their planar surfaces. The liquid is therefore exposed to the UV radiation over a total flow path of 240 inches, and because of this long length the bacteria within the exiting treated liquid is greatly reduced.

However, in order to reduce the bacteria in the liquid to the optimum quantity, it may be necessary to circulate the liquid being treated through enclosure 24 more than once. Circulating pump is therefore interconnected with input line 19 and output line 21. Circulating pump 17 can therefore be operated to independently control the fluid velocity within enclosure 24 and to effectively pass the liquid through UV exposure enclosure more than one time before it moves back into the main system. Under some flow conditions, it may be necessary to add check valve 23 to UV exposure apparatus 16 to properly direct the liquid flow.

It should be understood that the requirement for any such system is that the average exposure time of the liquid within the UV treatment apparatus must be such that the kill rate of bacteria effectively destroys at least as much bacteria as will be produced within the treatment time. This average exposure time can be reached either by using a flow path long enough to kill sufficient bacteria in a single pass or by recirculating liquid several times through a shorter path.

The parameters of the first embodiment of UV exposure apparatus 16 of FIG. 3 are listed below, assuming the liquid being sterilized has essentially no transmission of the UV wavelength being used for treatment. The application for such an embodiment yields a reduction of bacteria to less than one percent of the quantity entering, and is utilized in a system where the growth rate of bacteria is such that the quantity doubles every 1.6 hours.

Quantity of liquid in main system: 6500 gallons
Bacteria growth rate: 100% every 1.6 hours
Enclosure 24 size: 32 in. wide×36 in. long×12 in. high
Planar lamp 26 size: 30 in.×30 in.×0.5 in. thick
Lamp separation: 2 cm.
Lamp output: 125 mW/square cm.
Lamp wavelength: 282 nanometers
Lamp temperature rise: 20 degrees centigrade
Liquid flow rate in and out of enclosure 24:90 gpm
Liquid flow rate past lamps: 480 gpm
Typical pump 14 pressure required: 15 psi
Lamp power supply 18:10 kW at 5 kV at 150 kHz
Bacteria reduction factor: 99%
Reynolds number for the liquid flow between lamps: 30,000

Figure 4:
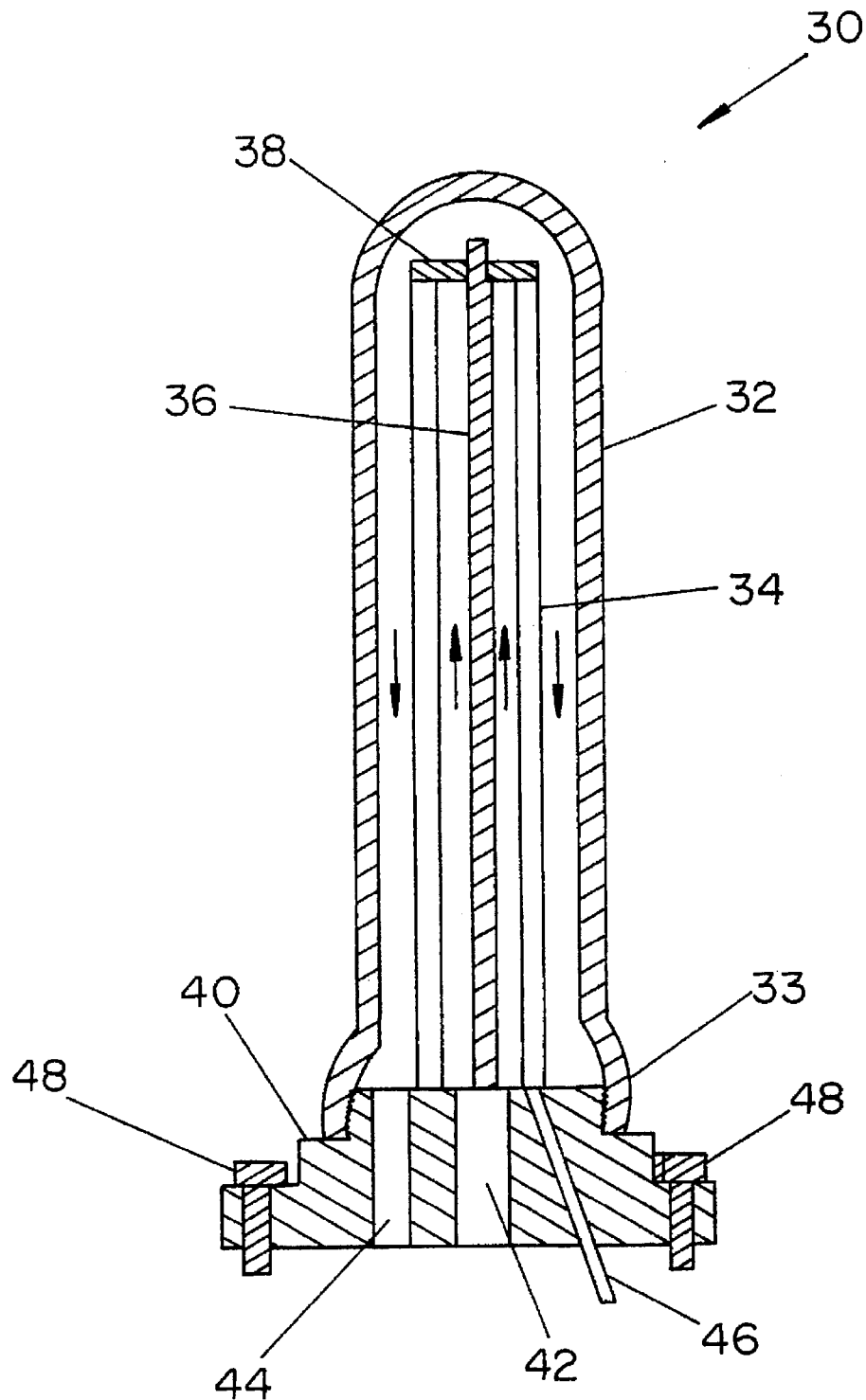
FIG. 4 is a cross section view of a single cylindrical UV exposure vessel which can be used in a series and parallel flow arrangement with several other identical devices to form an alternate embodiment of a UV exposure apparatus.

FIG. 4 is a cross section view of a single cylindrical UV treatment vessel 30 which can be used in a combined series and parallel flow arrangement with several other identical devices to form an alternate embodiment of UV treatment enclosure 24 shown in FIG. 3.

UV treatment vessel 30 is formed by cylindrical bell 32 which may be constructed of any suitable material such as stainless steel, and encloses cylindrical excimer lamp 34 which is mounted coaxial with cylindrical bell 32 and has a flow path through its central portion. Center support rod 36 holds end clamp 38, which is threaded onto rod 36, and clamps lamp 34 against base 40 onto which bell 32 is also threaded. Clamp 38 is formed as a web through which the treated liquid can flow, and base 40 includes liquid entry port 42 which feeds liquid to the center passage within lamp 34, and exit port 44 through which the treated liquid leaves UV treatment vessel 30. Electrical connections to lamp 34 are made through base 40 by wires 46.

The flow path through UV treatment vessel 30, which is typically approximately 72 inches long, is clearly much less that the approximately 240 inches of flow path available in regard to the embodiment of FIG. 3. However, it is a simple matter to connect several such UV treatment vessels in a series flow path, which would then yield approximately the same flow path length as the embodiment described for FIG. 3.

Similarly, although the flow path width of cylindrical UV treatment vessel 30 is much less than the flow path width with planar UV treatment vessel 24 of FIG. 3, multiple cylindrical vessels 30 can be arranged in parallel flow paths to furnish the same effective flow path width. Since the inside and outside circumferential surfaces of cylindrical lamp 34 average approximately eight inches, several such lamps in a parallel flow arrangement yield approximately the same flow path width as that of enclosure 24 of FIG. 3.

However, actually it is the lamp surface area, not the length or width of the path which determines the effect of the invention on bacteria, so that a series or parallel arrangement is more likely to be determined by the practical aspects of the piping and pump available for the system.

The series or parallel flow arrangement required for multiple cylindrical vessels can easily be accomplished by attaching base 40 to a flow manifold or pipes (not shown) by the use of bolts 48.

Despite the need for multiple cylindrical vessels 30 to furnish the equivalent of enclosure 24 of FIG.3, a substantial number of vessels 30 is far easier to maintain than a single large vessel. For instance, replacing lamp 34 involves only unscrewing bell 32 at threads 33 and web clamp 38, and the modular construction with several such vessels in a combined series or parallel arrangement permits bypassing the liquid flow from one or several units being serviced and therefore does not require the shutdown of the whole sterilization system. The use of series and parallel flow arrangements of cylindrical treatment vessels 30, therefore permits a great deal of versatility in the treatment options for liquids.

The parameters of the alternate embodiment of UV exposure vessel 30 of FIG. 4 are listed below for a series arrangement of eleven such lamps, assuming the liquid being sterilized has essentially no transmission of the UV wavelength being used for treatment.

Bell 32 size: 4.5 in. outside diameter×39 in. long

Lamp 34 size: 3.5 in. outside diameter in.×36 in. long

Lamp output: 125 mW/square cm.

Lamp wavelength: 282 nanometers

Lamp temperature rise: 20 degrees centigrade Liquid flow rate through all vessels 32:145 gpm Total lamp power supply 18:10 kW at 5 kV at 150 kHz Bacteria reduction factor: 99%

Reynolds number for the liquid flow: 30,000

Figure 5:
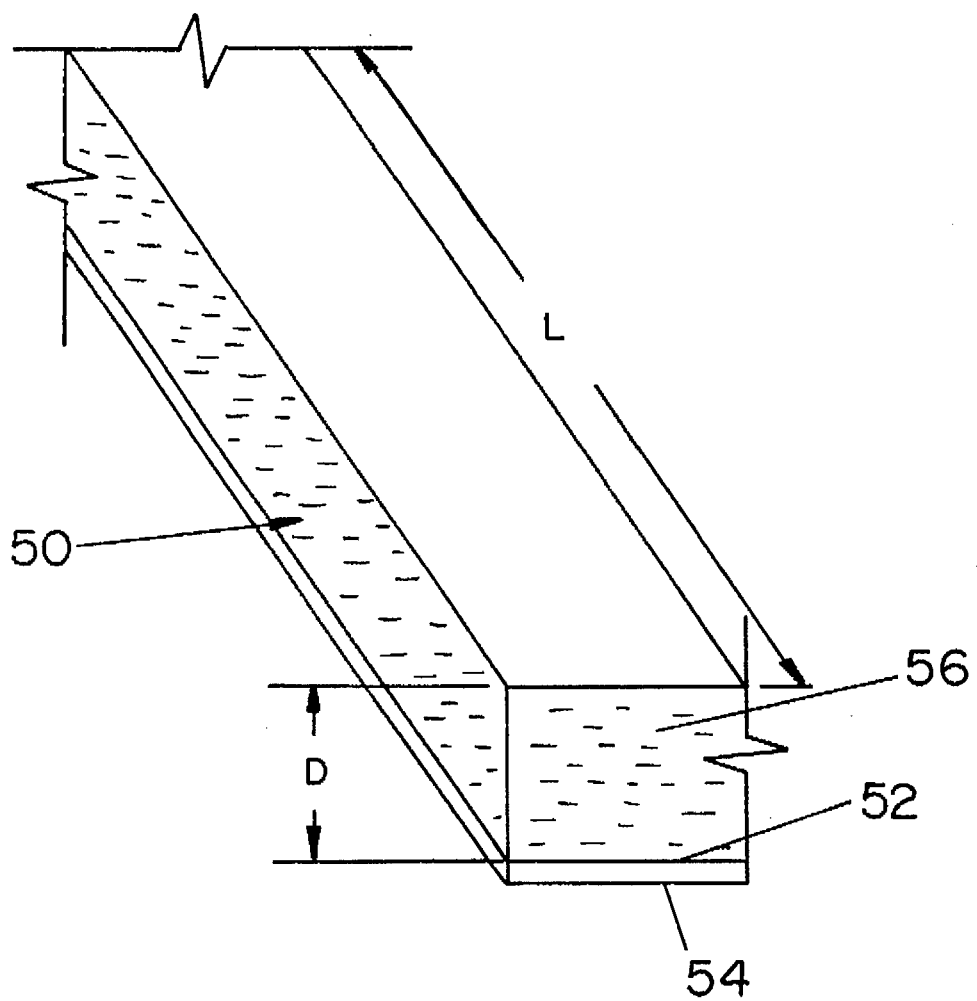
FIG. 5 is a perspective view of a part of a flow path in the simplest treatment structure of the invention, a single radiation exposure surface.

FIG. 5 is a perspective view of a portion 50 of a flow path in the simplest treatment structure of the invention, in which flow path 50 is exposed to a single radiation exposure surface 52. As previously discussed, radiation exposure surface 52 can typically be constructed as an excimer lamp radiating an essentially single wavelength of ultraviolet radiation from both its surfaces 52 and 54, so that a second flow path would also be exposed to lamp surface 54. As shown in FIG. 5 partial flow path 50 can be considered a small section along a flat plate or a small section of a curved surface such as a cylinder.

In either configuration the bacteria in an essentially opaque liquid is only killed at the layer of liquid 56 which is in direct contact with lamp surface 52. However, the turbulent flow of liquid 56 forces all the liquid in flow path 50 to contact lamp surface 52 if the liquid flows across the length L of flow path 50 for a long enough time. The time required is directly related to depth D and to the power density being radiated from lamp surface 52.

Experimentation has shown that, with a radiation power density of 125 mW/square cm, which is attainable from current excimer lamps, the bacteria in the layer in contact with the lamp will be killed in approximately 0.1 sec. Experimentation has also shown that when depth D of flow path 50 is 1.0 centimeter, with turbulent flow the bacteria will be reduced to one percent of the original value if the liquid is exposed to 125 mW/square cm of radiation for 36 seconds. This exposure time can be attained either with a single pass through a long flow path, or by the use of multiple passes through a shorter flow path.

This approach has led to the development of a simple formula to determine the volume of liquid in treatment flow path 50 (FIG. 5) which is required to treat an opaque fluid. The parameters in the formula are defined as follows.

T—volume of liquid in the treatment flow path (lamp treatment surface multiplied by depth D of flow path)

Kg—bacteria growth rate for the particular liquid in the system

Kr—bacteria reduction rate for the particular liquid with the lamp wavelength and power density selected V—liquid volume in the entire system to be treated Q—flow rate in the treatment apparatus The formula then becomes:

$$T = Kg \times V \times Q \text{ divided by } Kr\,(Q - Kg \times V)$$

The bacteria growth rate and the bacteria reduction rate, which are specific to particular bacteria being treated, can be determined experimentally with small quantities of the liquid to be treated if the rates are not available from biological reference material.

Ultimately the most important result of the present invention, regardless of the specific embodiment used, is the ability to sterilize opaque liquids without the use of any chemical biocides, and to do so at liquid flow rates which are applicable to many industrial applications.

It is to be understood that the forms of this invention as shown are merely preferred embodiments. Various changes may be made in the function and arrangement of parts; equivalent means may be substituted for those illustrated and described; and certain features may be used independently from others without departing from the spirit and scope of the invention as defined in the following claims.

For example, other configurations can be used for treatment vessels, such as the use of multiple cylindrical coaxial lamps of increasing diameter, thus furnishing a long serpentine flow path in a compact configuration in which the liquid flows back and forth between the cylindrical lamps. Furthermore, as the liquid opacity decreases and the depth of penetration of UV into the liquid increases, the flow path may be made shorter.

What is claimed as new and for which Letters Patent of the United States are desired to be secured is:

1. A method of destroying bacteria within a liquid which is opaque to ultraviolet radiation comprising:

establishing a flow path for an opaque liquid wherein at least a portion of the flow path is irradiated with ultraviolet radiation from two radiating surfaces which are concentric cylinders including an inner cylinder and an outer cylinder, with one radiating surface irradiating the region enclosed by the inner cylinder and the other radiating surface irradiating the region outside the outer cylinder, and the flow path passes through the inner cylinder and outside the outer cylinder; and moving the opaque liquid at a velocity which causes the liquid to move within the irradiated portion of the flow path in a turbulent flow pattern.

2. An apparatus to destroy bacteria within a liquid which is opaque to ultraviolet radiation comprising:

an enclosure with a liquid inlet and a liquid outlet;

at least one lamp mounted within the enclosure, the lamp including at least one radiating surface which produces ultraviolet radiation;

a structure enclosing a space defining a liquid flow path within the enclosure and between the liquid inlet and the liquid outlet, at least a portion of the liquid flow path being irradiated by being located in contact with and extending away from the radiating surface to receive direct exposure to the radiation from the radiating surface; and liquid pump means interconnected with the liquid flow path, the liquid pump means being capable of moving a liquid within the irradiated portion of the liquid flow path at a high enough velocity to cause liquid within the irradiated portion of the flow path to move in a turbulent flow pattern without being influenced by deflecting surfaces, so that liquid located remote from the radiating surface is brought into contact with the radiating surface by the turbulent flow pattern wherein the lamp includes two radiating surfaces which are concentric cylinders.

3. The apparatus of claim 2 wherein the lamp includes two radiating surfaces which are concentric cylinders including an inner cylinder and an outer cylinder, with one radiating surface irradiating the region enclosed by the inner cylinder and the other radiating surface irradiating the region outside the outer cylinder.

4. The apparatus of claim 2 wherein the lamp includes two radiating surfaces which are concentric cylinders including an inner cylinder and an outer cylinder, with one radiating surface irradiating the region enclosed by the inner cylinder and the other radiating surface irradiating the region outside the outer cylinder, and the flow path passes through the inner cylinder and outside the outer cylinder.

5. An apparatus to destroy bacteria within a liquid which is opaque to ultraviolet radiation comprising:

an enclosure having a liquid inlet and a liquid outlet and at least two opposing walls;

at least three planar excimer lamps mounted within the enclosure, each lamp including two parallel planar radiating surfaces which produce ultraviolet radiation, with the lamps being oriented so that the lamps are parallel and inter digitated and the radiating surfaces of the lamps are separated, one end of each of the lamps being attached to one of the opposing walls, each alternate lamp being attached to the other of the opposing walls so that spaces between the radiating surfaces of the lamps define a serpentine liquid flow path within the enclosure and between the liquid inlet and the liquid outlet, at least a portion of the liquid flow path being irradiated by being located in contact with and extending away from the radiating surfaces of two adjacent separated lamps to receive direct exposure to the radiation from the radiating surfaces; and liquid pump means interconnected with the liquid flow path, the liquid pump means being capable of moving a liquid within the irradiated portion of the liquid flow path at a high enough velocity to cause liquid within the irradiated portion of the flow path to move in a turbulent flow pattern without being influenced by deflecting surfaces, so that liquid located remote from the radiating surface is brought into contact with the radiating surface by the turbulent flow pattern.

6. The apparatus of claim 5 wherein the radiating surfaces produce ultraviolet radiation which is essentially monochromatic radiation.

7. The apparatus of claim 5 wherein the liquid flow path in contact with the radiating surfaces extends away from each radiating surface a maximum of two centimeters.

* * * * *